United States Patent [19]
Cooper

[11] Patent Number: 6,132,368
[45] Date of Patent: *Oct. 17, 2000

[54] MULTI-COMPONENT TELEPRESENCE SYSTEM AND METHOD

[75] Inventor: Thomas G. Cooper, Menlo Park, Calif.

[73] Assignee: Intuitive Surgical, Inc., Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/975,617

[22] Filed: Nov. 21, 1997

Related U.S. Application Data

[60] Provisional application No. 60/033,321, Dec. 12, 1996.

[51] Int. Cl.$^7$ .................................................. A61B 1/00
[52] U.S. Cl. ........................ 600/102; 606/130; 606/1
[58] Field of Search .................................. 600/101, 102, 600/114, 121, 122; 606/1, 130; 128/849–856

[56] References Cited

U.S. PATENT DOCUMENTS

| | | |
|---|---|---|
| 4,281,447 | 8/1981 | Miller et al. . |
| 4,332,066 | 6/1982 | Hailey et al. . |
| 4,486,928 | 12/1984 | Tucker et al. . |
| 4,500,065 | 2/1985 | Hennekes et al. . |
| 4,512,709 | 4/1985 | Hennekes et al. . |
| 4,706,372 | 11/1987 | Ferrero et al. . |
| 4,710,093 | 12/1987 | Zimmer et al. . |
| 4,793,053 | 12/1988 | Zuccaro et al. . |
| 4,809,747 | 3/1989 | Choly et al. . |
| 4,830,569 | 5/1989 | Jannborg . |
| 4,832,198 | 5/1989 | Alikhan . |
| 4,943,939 | 7/1990 | Hoover . |
| 4,979,949 | 12/1990 | Matsen, III et al. . |
| 4,996,975 | 3/1991 | Nakamura . |
| 5,018,266 | 5/1991 | Hutchinson et al. . |
| 5,078,140 | 1/1992 | Kwoh . |
| 5,143,453 | 9/1992 | Weynant née Girones . |
| 5,154,717 | 10/1992 | Matsen, III et al. . |
| 5,174,300 | 12/1992 | Bales et al. . |
| 5,184,601 | 2/1993 | Putman . |
| 5,217,003 | 6/1993 | Wilk . |
| 5,221,283 | 6/1993 | Chang . |
| 5,236,432 | 8/1993 | Matsen, III et al. . |
| 5,255,429 | 10/1993 | Nishi et al. . |
| 5,257,998 | 11/1993 | Ota et al. . |
| 5,271,384 | 12/1993 | McEwen et al. . |
| 5,294,209 | 3/1994 | Naka et al. . |
| 5,305,203 | 4/1994 | Raab . |
| 5,312,212 | 5/1994 | Naumec . |
| 5,313,935 | 5/1994 | Kortenbach et al. . |
| 5,337,732 | 8/1994 | Grundfest et al. . |
| 5,343,385 | 8/1994 | Joskowicz et al. . |
| 5,354,314 | 10/1994 | Hardy et al. . |
| 5,355,743 | 10/1994 | Tesar . |

(List continued on next page.)

FOREIGN PATENT DOCUMENTS

| | | |
|---|---|---|
| WO 93/13916 | 7/1993 | WIPO . |
| WO 94/26167 | 11/1994 | WIPO . |
| WO 95/16396 | 6/1995 | WIPO . |
| WO 95/30964 | 11/1995 | WIPO . |
| WO 96/39944 | 12/1996 | WIPO . |

*Primary Examiner*—John P. Leubecker
*Attorney, Agent, or Firm*—Townsend and Townsend and Crew LLP; Mark D. Barrish, Esq.

[57] ABSTRACT

The present invention provides systems and methods for performing robotically-assisted surgical procedures on a patient. In particular, a three-component surgical system is provided that includes a non-sterile drive and control component, a sterilizable end effector or surgical tool and an intermediate connector component that includes mechanical elements for coupling the surgical tool with the drive and control component and for transferring motion and electrical signals therebetween. The drive and control component is shielded from the sterile surgical site, the surgical tool is sterilizable and disposable and the intermediate connector is sterilizable and reusable. In this manner, the intermediate connector can be sterilized after a surgical procedure without damaging the motors or electrical connections within the drive and control component of the robotic system.

41 Claims, 9 Drawing Sheets

U.S. PATENT DOCUMENTS

| | | |
|---|---|---|
| 5,359,993 | 11/1994 | Slater et al. . |
| 5,372,147 | 12/1994 | Lathrop, Jr. et al. . |
| 5,397,323 | 3/1995 | Taylor . |
| 5,399,951 | 3/1995 | Lavallee et al. . |
| 5,400,267 | 3/1995 | Denen et al. . |
| 5,402,801 | 4/1995 | Taylor . |
| 5,417,210 | 5/1995 | Funda et al. . |
| 5,427,097 | 6/1995 | Depp . |
| 5,451,368 | 9/1995 | Jacob . |
| 5,624,398 | 4/1997 | Smith et al. . |
| 5,631,973 | 5/1997 | Green . |
| 5,649,956 | 7/1997 | Jensen et al. . |
| 5,695,501 | 12/1997 | Carol et al. ............................. 606/130 |
| 5,792,135 | 8/1998 | Madhani et al. . |
| 5,800,423 | 9/1998 | Jensen . |
| 5,855,583 | 1/1999 | Wang et al. ............................. 606/130 |
| 5,876,325 | 3/1999 | Mizuno et al. ........................ 600/102 |

MULTI-COMPONENT TELEPRESENCE SYSTEM AND METHOD

CROSS-REFERENCE TO RELATED APPLICATIONS

This application is a continuation of, and claims the benefit of priority from, U.S. Provisional Patent Application Ser. No. 60/033,321, filed Dec. 12, 1996, the full disclosure of which is hereby incorporated by reference.

BACKGROUND OF THE INVENTION

This invention relates to robotically-assisted surgical manipulators and more particularly to systems and methods for performing telerobotic surgical procedures on a patient while providing the surgeon with the sensation of physical presence at the surgical site.

In robotically-assisted or telerobotic surgery, the surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each perform various functions for the surgeon, e.g., holding or driving a needle, grasping a blood vessel, or dissecting, cauterizing or coagulating tissue.

This new method of performing telerobotic surgery through remote manipulation has, of course, created many new challenges. One such challenge results from the fact that a portion of the electromechanical surgical manipulator will be in direct contact with the surgical instruments, and will also be positioned adjacent the operation site. Accordingly, the surgical manipulator may become contaminated during surgery and is typically disposed of or sterilized between operations. Of course, from a cost perspective, it would be preferable to sterilize the device. However, the servo motors, sensors, encoders and electrical connections that are necessary to robotically control the motors typically cannot be sterilized using conventional methods, e.g., steam, heat and pressure or chemicals, because they would be damaged or destroyed in the sterilization process.

Yet another challenge with telerobotic surgery systems is that a surgeon will typically employ a large number of different surgical instruments during a procedure. Since the number of instrument holders are limited due to space constraints and cost, many of these surgical instruments will be attached and detached from the same instrument holder a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the holder and exchange them with other surgical tools.

What is needed, therefore, are improved telerobotic systems and methods for remotely controlling surgical instruments at a surgical site on a patient. These systems and methods should be configured for easy sterilization so that they can be reused after the components have been contaminated during an operation. In addition, these systems and methods should be designed to minimize instrument exchange time during the surgical procedure.

SUMMARY OF THE INVENTION

The present invention provides systems and methods for performing remote, robotically-assisted surgical procedures on a patient while providing the surgeon with the sensation of physical presence at the surgical site (i.e., telepresence). In particular, a three-component surgical system is provided that includes a non-sterile drive and control component, a sterilizable end effector or surgical tool and an intermediate connector component that includes mechanical elements for coupling the surgical tool with the drive and control component, and for transferring motion from the drive component to the surgical tool. The drive and control component is shielded from the sterile surgical site, the surgical tool is sterilizable and disposable and the intermediate connector is sterilizable and reusable. In this manner, the intermediate connector can be sterilized after a surgical procedure without damaging the motors or electrical connections within the drive and control component of the robotic system.

The drive and control component of the present invention generally includes the drive actuators, e.g., motors, gears or pulleys, etc., and positioning devices that are necessary to articulate the surgical tool at the surgical site. In addition, the drive and control component will usually include the encoders and electrical connectors required to couple the component to a servomechanism to form a master/slave telerobotic surgical system. In a specific configuration of the invention, this component comprises a manipulator assembly having a drive assembly and a multiple degree of freedom manipulator arm. The arm and drive assembly are covered by a sterile drape to effectively shield these components from the sterile surgical field during the operation. In this way, the portion of the system including motors, encoders and fragile electronics does not have to be sterilized because it is separated from the sterile field surrounding the surgical site.

The intermediate connector includes a sterile adaptor that extends through an opening in the sterile drape to couple the sterile surgical tool with the manipulator arm. The adaptor includes a plurality of motion and electrical feed-throughs for articulating the surgical tool, and for sending electrical signals to and from the tool, e.g., force and torque feedback signals, etc. In one configuration, the intermediate component includes a scope adaptor for coupling a viewing scope, such as an endoscope coupled to a camera mount and a camera, to the manipulator arm. In another configuration, the intermediate connector includes a surgical instrument assembly coupled to the sterile adaptor. The surgical instrument assembly will usually include a surgical tool, which may comprise a variety of articulated tools with end effectors, such as jaws, scissors, graspers, needle holders, micro dissectors, staple appliers, tackers, suction irrigation tools, clip appliers, or non-articulated tools, such as cutting blades, cautery probes, irrigators, catheters or suction orifices.

In a preferred configuration, the surgical instrument assembly will further include a wrist unit for removably coupling the surgical tool to the adaptor on the manipulator assembly. The wrist unit comprises an elongate shaft with a distal wrist coupled to the surgical tool for providing articulation of the tool about the distal wrist. During a surgical procedure, the telerobotic system will usually include a variety of surgical instrument assemblies, each having a wrist unit with a different surgical tool attached. The wrist units can be quickly and easily coupled and decoupled from the manipulator assemblies to facilitate instrument exchange during the procedure. In an exemplary embodiment, the wrist unit is reposable, and it includes a mechanism for counting the number of times the wrist unit is used to inhibit further use of the unit.

The manipulator assembly provides a plurality of degrees of freedom to the wrist unit and surgical tool including pitch and yaw movement of the tool about the wrist, rotation about the wrist shaft axis, axial movement and articulation of the end effector on the surgical tool. In addition, the manipulator assembly preferably provides pitch and yaw motion of the wrist unit and the surgical tool about axes perpendicular to the wrist shaft. The motors of the drive assembly are located proximally from the arm and the intermediate component, which facilitates cleaning, decreases the cost of manufacturing the assembly and decreases the inertia of the surgical tool and wrist unit. In a preferred configuration, the manipulator assembly will include a remote center positioning device, such as a parallelogram linkage, for constraining motion of the wrist unit and/or surgical tool about a desired fixed center of rotation. This fixed center of rotation may be located on the wrist unit shaft, at the distal wrist, or in endoscopic procedures, coincident with the entry incision within the patient's body.

In an exemplary embodiment, the three-component surgical manipulator of the present invention is part of a telerobotic system in which the surgeon manipulates input control devices and views the operation via a displayed image from a location remote from the patient. The system includes a servomechanism coupled to one or more manipulator assemblies to control the wrist units and surgical tools in response to the surgeon's manipulation of the input control devices. Position, force, and tactile feedback sensors (not shown) may also be employed to transmit position, force, and tactile sensations from the surgical tools back to the surgeon's hands as he/she operates the telerobotic system. A monitor is coupled to the viewing scope such that the displayed image of the surgical site is provided adjacent the surgeon's hands. The image is preferably oriented so that the surgeon feels that he or she is actually looking directly at the operating site. This configuration provides the surgeon with telepresence, or the perception that the input control devices are integral with the surgical tools.

DESCRIPTION OF THE PREFERRED EMBODIMENT

The present invention provides a multi-component system and method for performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention is particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master to form a telepresence system with force reflection. A description of a suitable slave-master system can be found in co-pending patent application Ser. No. 08/517,053, filed Aug. 21, 1995 (Attorney Docket No. 287-004810), the complete disclosure of which is incorporated herein by reference.

Figure 1:
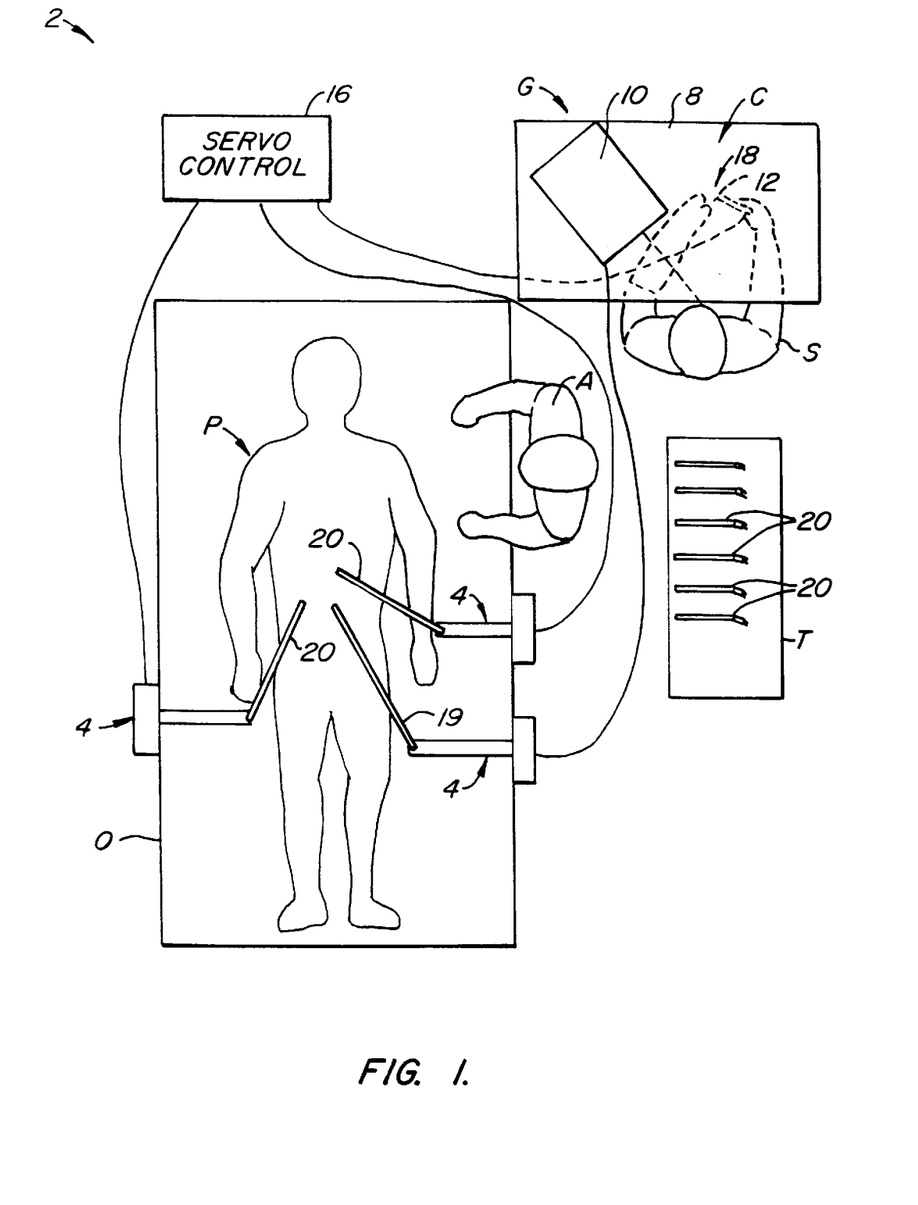
FIG. 1 is a schematic view of an operating room, illustrating a telerobotic surgical system and method according to the present invention.

Referring to the drawings in detail, wherein like numerals indicate like elements, a telerobotic surgical system 2 is illustrated according to the present invention. As shown in FIG. 1, telerobotic system 2 generally includes one or more surgical manipulator assemblies 4 mounted to or near an operating table O, and a control assembly 6 for allowing the surgeon S to view the surgical site and to control the manipulator assemblies 4. The system 2 will also include one or more viewing scope assemblies 19 and a plurality of surgical instrument assemblies 20 adapted for being removably coupled to manipulator assemblies 4 (discussed in detail below). Telerobotic system 2 usually includes at least two manipulator assemblies 4 and preferably three manipulator assemblies 4. Of course, the exact number of manipulator assemblies 4 will depend on the surgical procedure and the space constraints within the operating room among other factors. As discussed in detail below, one of the assemblies 4 will typically operate a viewing scope assembly 19 (in endoscopic procedures) for viewing the surgical site, while the other manipulator assemblies 4 operate surgical instruments 20 for performing various procedures on the patient P.

Control assembly 6 may be located at a surgeon's console C which is usually located in the same room as operating table O so that the surgeon may speak to his/her assistant(s) A and directly monitor the operating procedure. However, it will be understood that the surgeon S can be located in a different room or a completely different building from the patient P. Control assembly 6 generally includes a support 8, a monitor 10 for displaying an image of the surgical site to the surgeon S, and one or more controller(s) 12 for controlling manipulator assemblies 4. Controller(s) 12 may include a variety of input devices, such as joysticks, gloves, triggerguns, hand-operated controllers, voice recognition devices or the like. Preferably, controller(s) 12 will be provided with the same degrees of freedom as the associated surgical instrument assemblies 20 to provide the surgeon with telepresence, or the perception that the controller(s) 12 are integral with the instruments 20 so that the surgeon has a strong sense of directly controlling instruments 20. Position, force, and tactile feedback sensors (not shown) may also be employed on instrument assemblies 20 to transmit position, force, and tactile sensations from the surgical instrument back to the surgeon's hands as he/she operates the telerobotic system. One suitable system and method for providing telepresence to the operator is described in co-pending patent application Ser. No. 08/517,053, filed Aug. 21, 1995, (Attorney Docket No. 0287S-004810), which has previously been incorporated herein by reference.

Monitor 10 will be suitably coupled to the viewing scope assembly 19 such that an image of the surgical site is provided adjacent the surgeon's hands on surgeon console 6. Preferably, monitor 10 will display an inverted image on a display 18 that is oriented so that the surgeon feels that he or she is actually looking directly down onto the operating site. To that end, an image of the surgical instruments 20 appears to be located substantially where the operator's hands are located even though the observation points (i.e., the endoscope or viewing camera) may not be from the point of view of the image. In addition, the real-time image is preferably transformed into a perspective image such that the operator can manipulate the end effector and the hand control as if viewing the workspace in substantially true presence. By true presence, it is meant that the presentation of an image is a true perspective image simulating the viewpoint of an operator that is physically manipulating the surgical instruments 20. Thus, a controller (not shown) transforms the coordinates of the surgical instruments 20 to a perceived position so that the perspective image is the image that one would see if the camera or endoscope was located directly behind the surgical instruments 20. A suitable coordinate transformation system for providing this virtual image is described in patent application Ser. No. 08/239,086, filed May 5, 1994, (Attorney Docket No. 0287S-003300), the complete disclosure of which is incorporated herein by reference.

As shown in FIG. 1, a servomechanism 16 is provided for transferring the mechanical motion of controllers 12 to manipulator assemblies 4. Servomechanism 16 may be separate from, or integral with manipulator assemblies 4. Servomechanism 16 will usually provide force and torque feedback from the surgical instruments 20 to the handoperated controllers 12. In addition, servomechanism 16 will include a safety monitoring controller (not shown) that may freeze or at least inhibit all robot motion in response to recognized conditions (e.g., exertion of excessive force on the patient, "running away" of the manipulator assemblies 4, etc.). The servomechanism preferably has a servo bandwidth with a 3 dB cut off frequency of at least 10 hz so that the system can quickly and accurately respond to the rapid hand motions used by the surgeon. To operate effectively with this system, manipulator assemblies 4 have a relatively low inertia and the drive motors 170 (see FIG. 8) have relatively low ratio gear or pulley couplings. Any suitable conventional or specialized servomechanism may be used in the practice of the present invention, with those incorporating force and torque feedback being particularly preferred for telepresence operation of the system.

Figure 7:
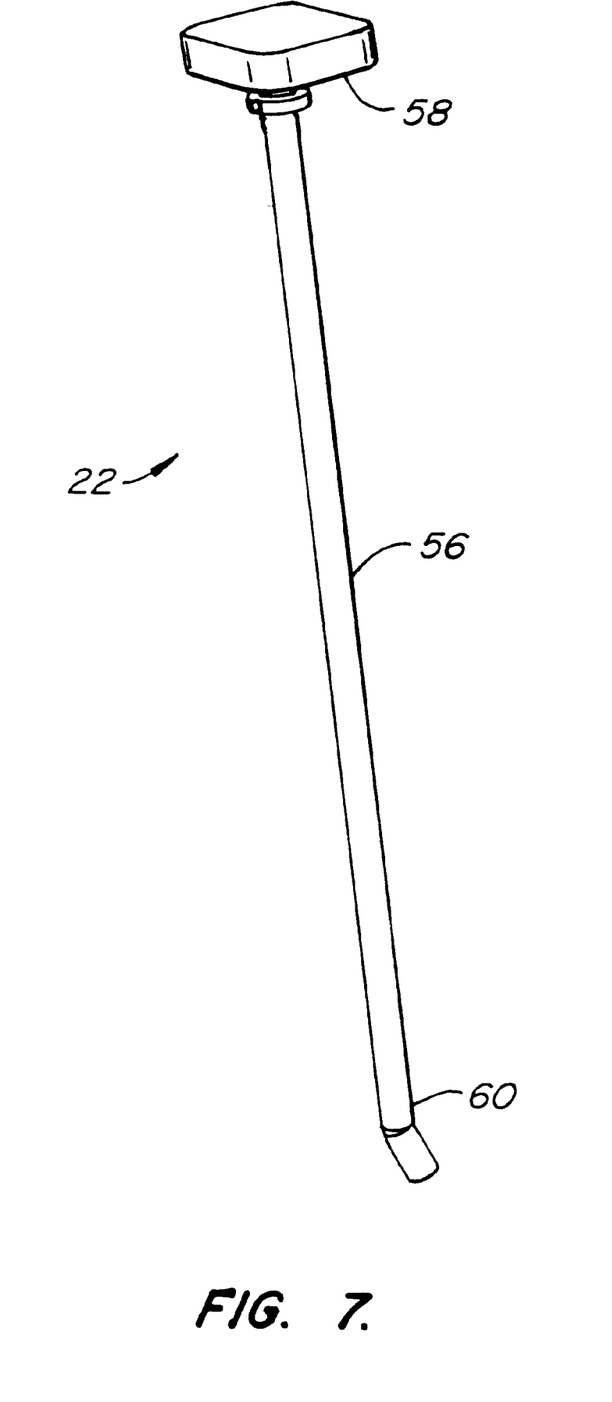
FIG. 7 is a perspective view of the wrist unit according to the present invention.

Referring to FIG. 7, surgical instrument assemblies 20 each include a wrist unit 22 and a surgical tool 24 removably attached to wrist unit 22. As discussed in detail below, each wrist unit 22 generally includes an elongate shaft 56 having a proximal cap 58 and a distal wrist 60 pivotally coupled to surgical tool 24. Each wrist unit 22 is substantially the same, and will have different or the same surgical tools 24 attached thereto, depending on the requirements of the surgical procedure. Alternatively, wrist units 22 may have specialized wrists 60 designed for individual surgical tools 24 so that the wrist units 22 may be used with conventional tools 24. As shown in FIG. 1, the instrument assemblies 20 are usually assembled onto a table T or other suitable support adjacent the operating table O. According to a method of the present invention (described below), wrist units 22 and their associated surgical tools 24 can be quickly exchanged during the surgical procedure by coupling and decoupling wrist unit shafts 56 from manipulator assemblies 4.

Figure 2:
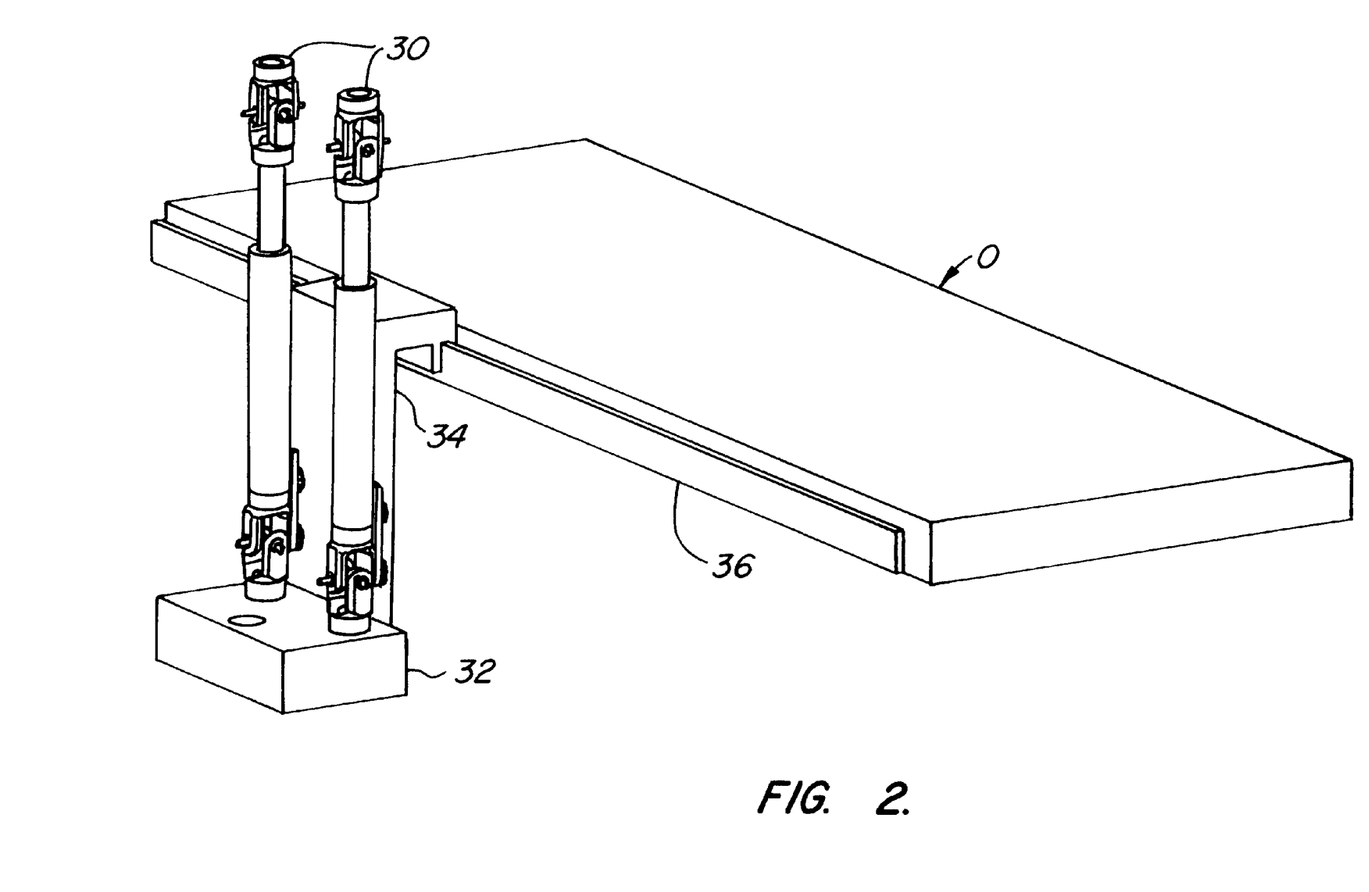
FIG. 2 is an enlarged view of the operating room of FIG. 1 illustrating a pair of mounting joints coupled to an operating table according to the present invention.

Referring to FIG. 2, each manipulator assembly 4 is preferably mounted to operating table O by a mounting joint 30. Mounting joints 30 provide a number of degrees of freedom (preferably at least 5) to assemblies 4, and they include a brake (not shown) so that assemblies 4 can be fixed at a suitable position and orientation relative to the patient. Joints 30 are mounted to a receptacle 32 for mounting joints 30 to operating table O, and for connecting each manipulator assembly 4 to servomechanism 16. In addition, receptacle 32 may connect joints 30 to other systems, such as an RF electrical power source, a suction-irrigation system, etc. Receptacle 32 includes a mounting arm 34 that is slidably disposed along an outer rail 36 of operating table O. Of course, manipulator assemblies 4 may be positioned over the operating table O with other mechanisms. For example, the system may incorporate a support system (coupled to the ceiling or a wall of the operating room) that moves and holds one or more manipulator assemblies 4 over the patient.

Referring now to FIGS. 3–8, manipulator assembly 4 will be described in further detail. Manipulator assembly 4 is a three-component apparatus that includes a non-sterile drive and control component, a sterilizable end effector or surgical tool (i.e., surgical instrument assembly 20) and an intermediate connector component. The intermediate connector includes mechanical elements for coupling the surgical tool 24 with the drive and control component, and for transferring motion from the drive component to the surgical tool 24. As shown in FIG. 3B, the drive and control component generally includes a drive assembly 40 and a multiple degree of freedom robotic arm 42 coupled to a mounting bracket 44, which is adapted for mounting onto mounting joints 30 (FIG. 2). Preferably, drive assembly 40 and robotic arm 42 are pivotally coupled to bracket 44 about an X-axis, which extends through a remote center of spherical rotation 45 (see FIG. 8, discussed in further detail below). Manipulator assembly 4 further includes a forearm assembly 46 fixed to a distal end 48 of arm 42, and a wrist unit adaptor 52 coupled to forearm assembly 46 for mounting wrist unit 22 and surgical tool 24 to manipulator assembly 4.

For endoscopic procedures, manipulator assembly 4 additionally includes a cannula adaptor 64 attached to a lower portion of forearm 46 for mounting a cannula 66 to manipulator assembly 4. Alternatively, cannula 66 may be an integral cannula (not shown) that is built into forearm assembly 46 (i.e., non-removable). Cannula 66 may include a force sensing element (not shown), such as a strain gauge or force-sensing resistor, mounted to an annular bearing within cannula 66. The force sensing bearing supports surgical tool 24 during surgery, allowing the tool to rotate and move axially through the central bore of the bearing. In addition, the bearing transmits lateral forces exerted by the surgical tool 24 to the force sensing element, which is connected to servomechanism 16 for transmitting these forces to controller(s) 12. In this manner, forces acting on surgical tools 24 can be detected without disturbances from forces acting on cannula 66, such as the tissue surrounding the surgical incision, or by gravity and inertial forces acting on manipulator assembly 4. This facilitates the use of manipulator assembly in a robotic system because the surgeon will directly sense the forces acting against the surgical tool 24.

Figure 3A:
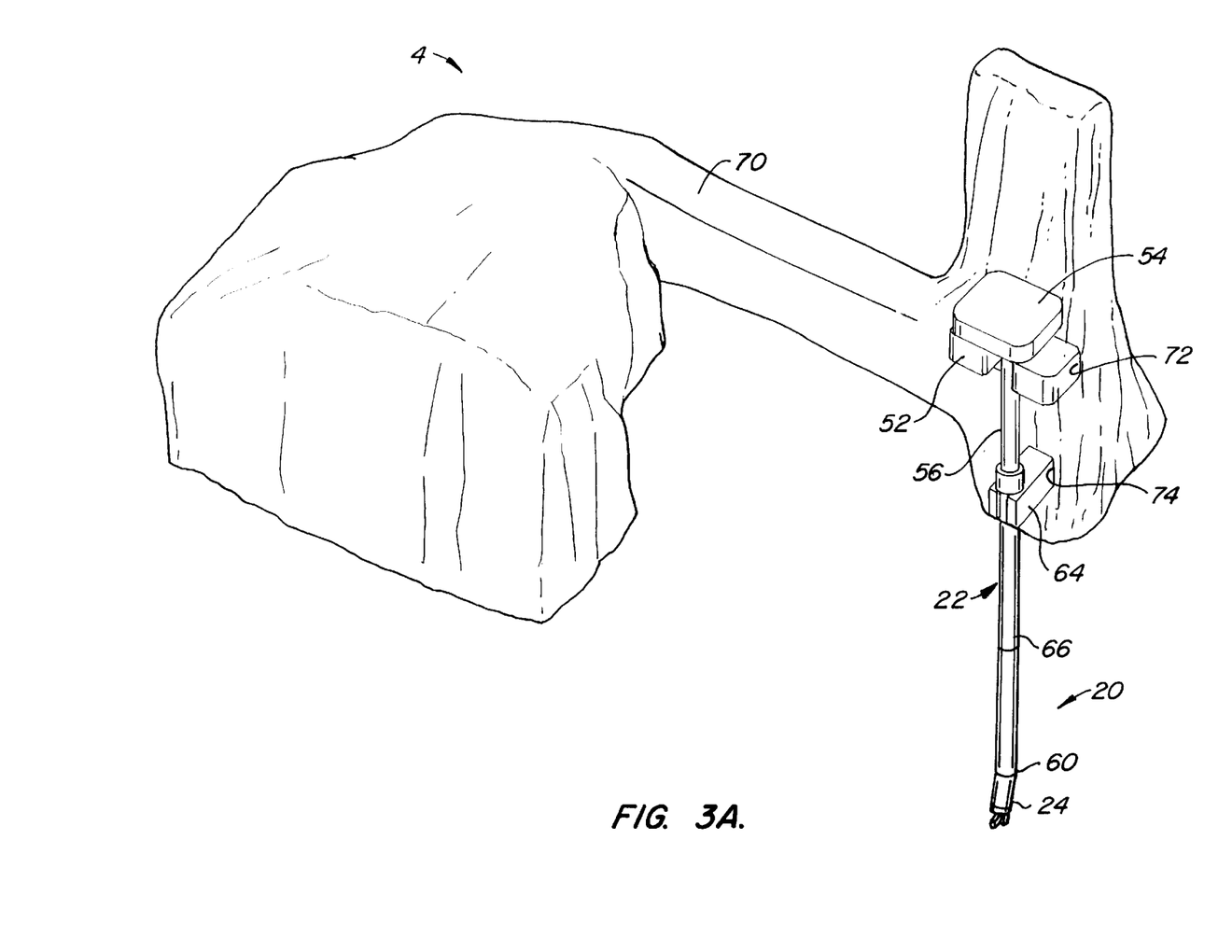
FIG. 3A is a perspective view of a robotic surgical manipulator according to the present invention that is partially covered by a sterile drape.

As shown in FIG. 3A, manipulator assembly 4 further includes a sterile drape 70 sized to cover substantially the entire manipulator assembly 4. Drape 70 has a pair of holes 72, 74 sized and arranged so that wrist unit adaptor 52 and cannula adaptor 64 may extend through holes 72, 74 to mount wrist unit 22 and cannula 66 to manipulator assembly 4. Sterile drape 70 comprises a material configured to effectively shield manipulator assembly 4 from the surgical site so that most of the components of assembly 4 (i.e., arm 42, drive assembly 40 and forearm assembly 46) do not have to be sterilized prior to, or following the surgical procedure.

As shown in FIG. 3A, wrist unit adaptor 52 and cannula adaptor 64 extend through holes 72, 74 of drape 70 so that forearm assembly 46 and the remainder of manipulator assembly 4 remain shielded from the patient during the procedure. Wrist unit adaptor 52 and cannula adaptor 64 are preferably manufactured as reusable components that will be sterilized because these components extend into the sterile field of the surgical site. Wrist unit and cannula adapters 52, 64 may be sterilized by normal methods, i.e., steam, heat and pressure, chemicals and the like. Referring again to FIG. 3B, wrist unit adaptor 52 includes an opening 80 for receiving shaft 56 of wrist unit 22. As discussed in detail below, shaft 56 can be laterally urged through opening 80 and snap-fit into adaptor 52 such that the non-exposed portion of wrist unit adaptor 52 remains sterile (i.e., remains on the sterile side of drape 70 opposite the sterile field). Wrist unit adaptor 52 may also include a latch (not shown) for securing wrist unit 22 therein. Similarly, cannula adaptor 64 includes an opening 82 for snap fitting cannula 66 thereto such that the non-exposed portion of adaptor 64 remains sterile during the surgical procedure.

Figure 4:
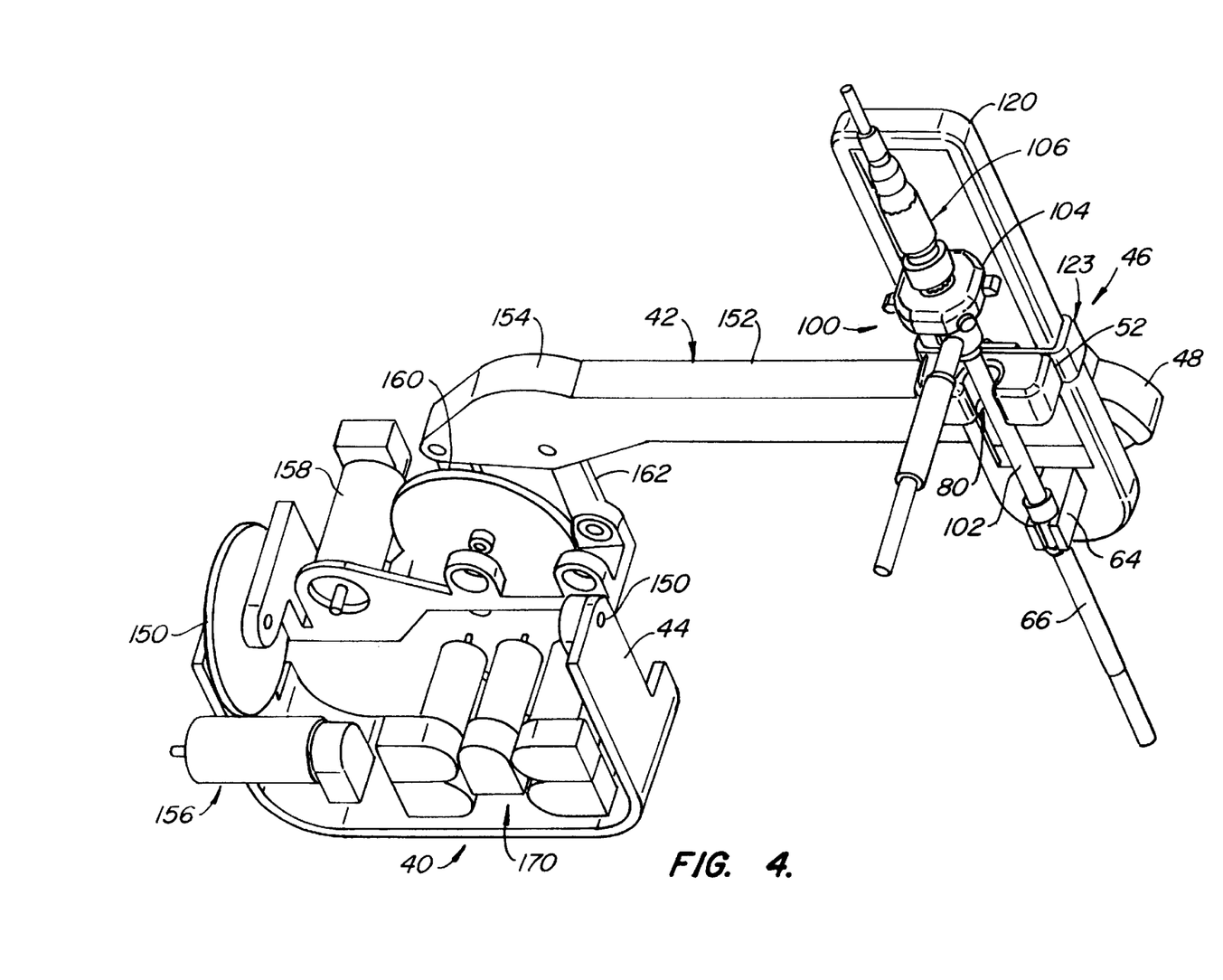
FIG. 4 illustrates the robotic surgical manipulator of FIGS. 3A–3B incorporating a camera and endoscope for viewing the surgical site.

As shown in FIG. 4, wrist unit adaptor 52 may also be configured to receive a viewing scope 100 for viewing the surgical site. For endoscopic procedures, viewing scope 100 can be a conventional endoscope, which typically includes a rigid, elongated tube 102 containing a lens system (not shown) and a camera mount 104 at the proximal end of the tube 102. A small video camera 106 is preferably attached to the camera mount 104 and connected to video monitor 10 to provide a video image of the procedure. Preferably, the scope 100 has a distal end (not shown) configured to allow lateral or angled viewing relative to tube 102. The viewing scope may also have a guidable tip that can be deflected or rotated by manipulating an actuator on a proximal end of tube 102. This type of scope is commercially available from Baxter Healthcare Corp. of Deerfield, Ill., or Origin Medsystems, Inc. of Menlo Park, Calif.

As shown in FIG. 4, viewing scope 100 further includes a scope adaptor 110 for coupling viewing scope 100 to wrist unit adaptor 52. Scope adaptor 110 is sterilizable, ETO and autoclavable, and it includes a plurality of motion feedthroughs (not shown) for transferring motion from drive assembly 40 to scope 100. In the preferred configuration, the motion includes pitch and yaw motion, rotation about the Z-axis, and movement along the Z-axis.

Figure 5:
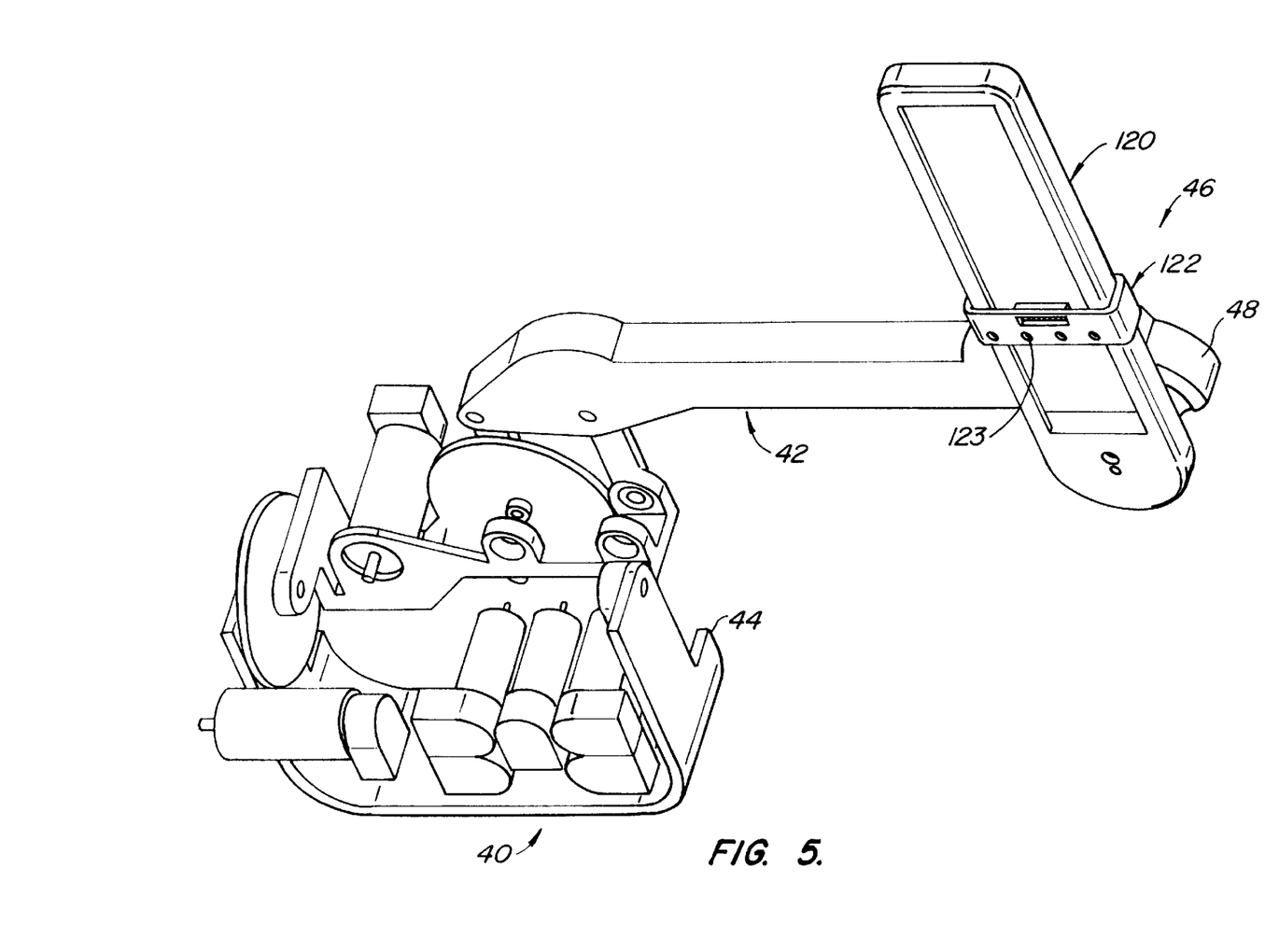
FIG. 5 is a partial view of the robotic manipulator of FIGS. 3A–3B, illustrating mechanical and electrical couplings between the arm and the wrist unit.
Figure 6:
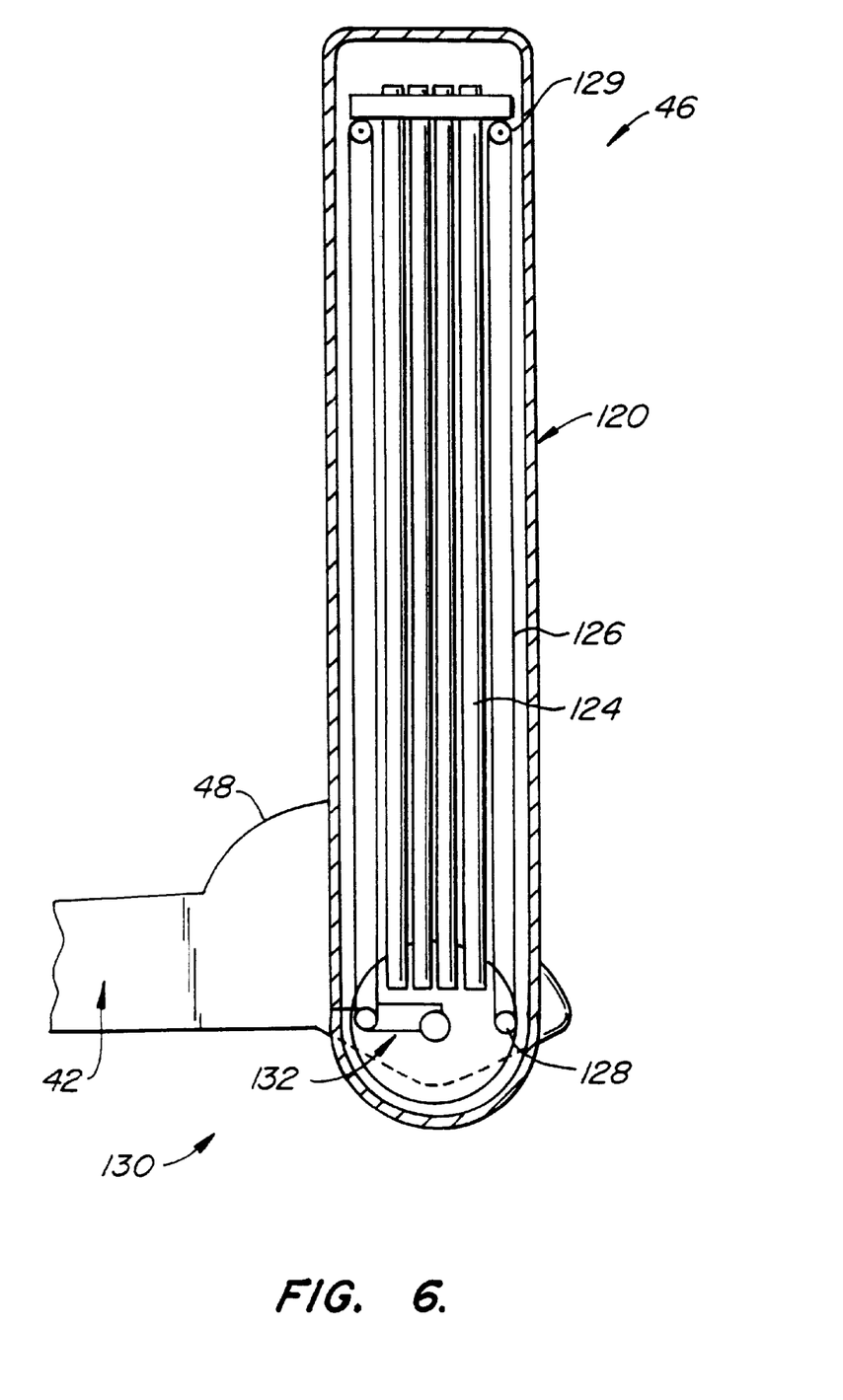
FIG. 6 is a partially cut-away sectional view of a forearm and a carriage of the manipulator of FIGS. 3a and 3B.

Referring now to FIGS. 5 and 6, forearm assembly 46 will be described in further detail. As shown in FIG. 5, forearm assembly 46 includes a housing 120 fixed to arm 42 and a movable carriage 122 slidably coupled to housing 120. Carriage 122 slidably mounts wrist unit adaptor 52 to housing 120 for moving wrist unit adaptor 52 and wrist unit 20 in the Z-direction. In addition, carriage 122 defines a number of openings 123 for transferring motion and electrical signals from forearm assembly 46 to wrist unit adaptor 52. As shown in FIG. 6, a plurality of rotatable shafts 124 are mounted within housing 120 for transferring motion from arm 42 through openings 123 to wrist unit adaptor 52 and wrist unit 22. Rotating shafts 124 preferably provide at least four degrees of freedom to wrist unit 22, including yaw and pitch motion of surgical tool 62 about wrist 60 of wrist unit 22, rotation of wrist unit 22 about the Z-axis and actuation of tool 62. Of course, the system may be configured to provide more or less degrees of freedom, if desired. Actuation of tool 62 may include a variety of motions, such as opening and closing jaws, graspers or scissors, applying clips or staples and the like. Motion of wrist unit 22 and tool 62 in the Z direction is provided by a pair of carriage cable drives 126 extending between rotatable pulleys 128, 129 on either end of forearm housing 120. Cable drives 126 function to move carriage 122 and wrist unit 22 in the Z direction relative to forearm housing 120.

As shown in FIG. 6, distal end 48 of arm 42 includes a coupling assembly 130 having a plurality of motion feedthroughs 132 for transferring motion from arm 42 to forearm assembly 46. In addition, coupling assembly 130 includes a number of electrical connectors (not shown) for transferring electrical signals from arm 42 to wrist unit 22. Similarly, wrist unit adaptor 52 includes a plurality of motion feedthroughs (not shown) and electrical connections (not shown) for transferring motion, and for sending and receiving electrical signals to and from wrist unit 22 (e.g., for sending and receiving force and torque feedback signals from the surgical site to controllers 12). The components on either side of coupling assembly 130 and wrist unit adaptor 52 have a finite range of motion. Usually, this range of motion will be at least 1 revolution and preferably greater than 1 revolution. These ranges of motion are aligned with each other when the forearm assembly 46 is mechanically coupled to the coupling assembly 130 and when wrist unit adaptor 52 is mechanically coupled to the forearm 46.

Referring to FIG. 7, wrist unit 22 will now be described in further detail. As shown, wrist unit 22 includes a hollow shaft 56 having a cap 58 attached to its proximal end and a wrist 60 attached to its distal end. Wrist 60 includes a coupling (not shown) for removably coupling a variety of surgical tools 62 to shaft 56. Shaft 56 is rotatably coupled to cap 58 for providing rotation of shaft 56 and tool 62 about the longitudinal axis of shaft 56 (i.e., the Z axis). Cap 58 houses a mechanism (not shown) for transferring motion from wrist unit adaptor 52 to drive cables (not shown) within shaft 56. The drive cables are suitably coupled to drive pulleys within shaft 56 to pivot tool 62 about wrist 60, and to actuate end effectors 140 on tool 62. Wrist 60 may also be operated by other mechanisms, such as differential gears, push-rods, or the like.

Tool 62 is removably coupled to wrist 60 of wrist unit 22. Tool 62 will preferably include an end effector 65 having a tactile sensor array (not shown) for providing tactile feedback to the surgeon. Tool 62 may include a variety of articulated tools, such as jaws, scissors, graspers, needle holders, micro dissectors, staple appliers, tackers, suction irrigation tools, clip appliers, that have end effectors driven by wire links, eccentric cams, push-rods or other mechanisms. In addition, tool 62 may comprise a non-articulated instrument, such as cutting blades, probes, irrigators, catheters or suction orifices. Alternatively, tool 62 may comprise an electrosurgical probe for ablating, resecting, cutting or coagulating tissue. In the latter embodiment, wrist unit 22 will include a conductive element, such as a proximal banana plug coupled to a lead wire or rod extending through shaft 56 to tool 62.

Figure 8:
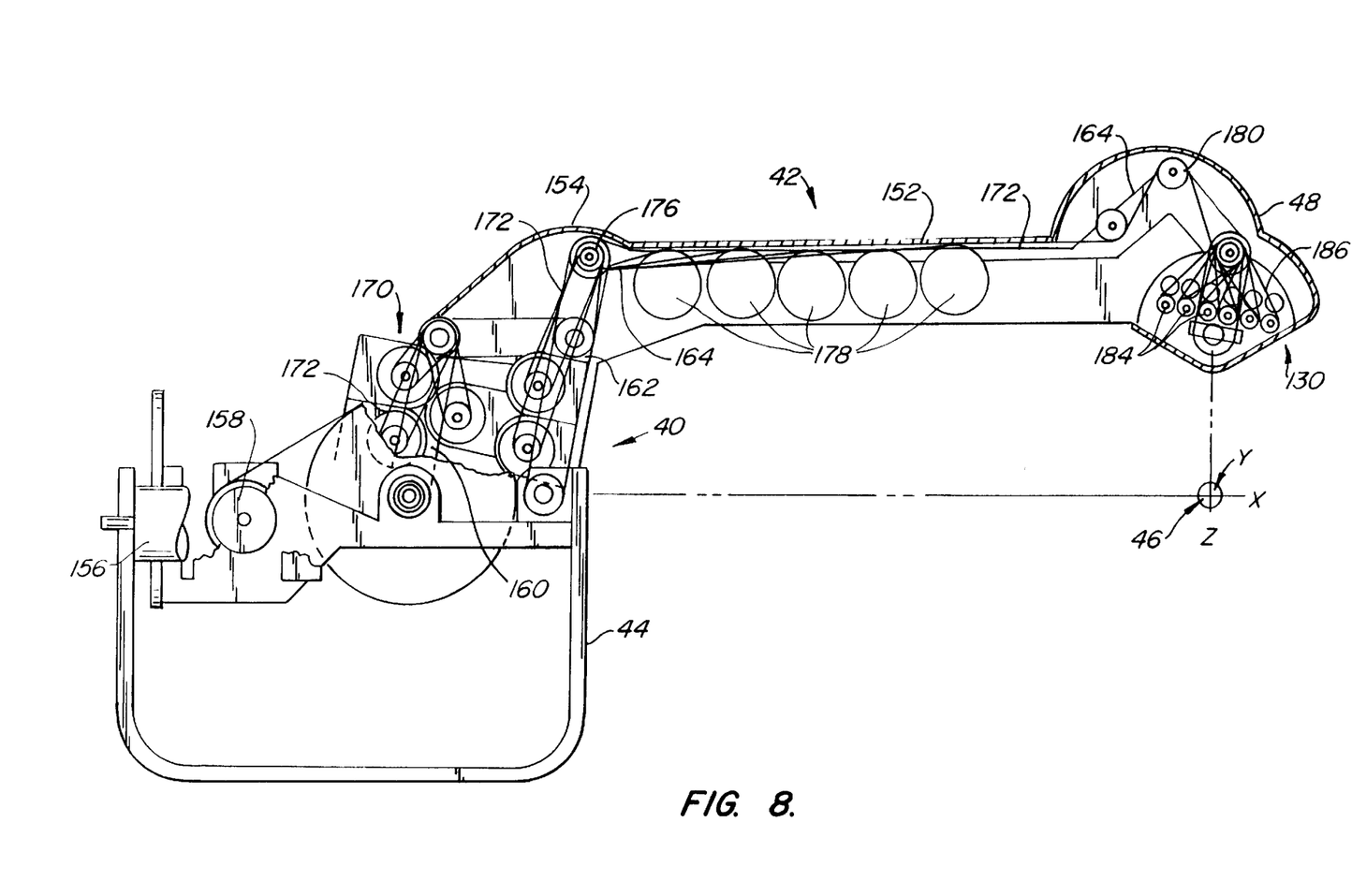
FIG. 8 is a side cross-sectional view of a portion of the robotic manipulator, illustrating the arm and the drive assembly.

Referring to FIGS. 4 and 8, a specific configuration of the drive and control component of the present invention (i.e., the robotic arm 42 and drive assembly 40) will be described in further detail. As discussed above, arm 42 and drive assembly 40 are rotatably coupled about a pair of pins 150 extending from mounting bracket 44. Arm 42 preferably comprises an elongate, substantially rigid body 152 with a distal end 48 coupled to forearm assembly 48 and a proximal end 154 pivotally coupled to drive assembly 40 and bracket 44 for rotation about pitch and yaw or the X and Y axes (note that the Y axis is perpendicular to the page and extends through point 45, see FIG. 8). Of course, arm 40 may have other configurations, such as an elbow arm (similar to the human arm), prismatic arm (straight extendable) or the like. A stationary yaw motor 156 is mounted to mounting bracket 44 for rotating arm 42 and drive assembly 40 about the X-axis. Drive assembly 40 also includes a pitch motor 158 coupled to arm 42 for rotating arm about the Y axis. A pair of substantially rigid linkage elements 160, 162 extend from bracket 44 to robotic arm 42 to pivotally couple arm 42 to bracket 44 about Y-axis. One of the linkage elements 160 is pivotally coupled to arm 42, and the other linkage element 162 is pivotally coupled to a third linkage element 164 extending parallel to arm 42. Preferably, robotic arm 42 is a channel shaped rigid element that at least partially houses the third linkage element 164. The linkage elements 160, 162 and 164 and arm 42 form a parallelogram linkage in which the members are connected together in a parallelogram for relative movement only in the plane formed by the members.

The Z-axis of wrist unit 22 held at the distal end 48 of arm 42 intersects the x axis of the parallelogram linkage described above. Wrist unit 22 has a remote center of spherical rotation about the position indicated by the numeral 45 in FIG. 8. Thus, the distal end of wrist unit 22 can be rotated about its own axis or the X and Y axes while the remote center of rotation 45 remains at the same location. A more complete description of a remote center positioning device can be found in co-pending application Ser. No. 08/504,301, filed Jul. 20, 1995 (Attorney Work Docket 287-002940), the complete disclosure of which is incorporated herein by reference. It should be noted that arm 42 and drive assembly 40 may be used with a broad range of positioning devices other than that described above and shown in FIG. 8, such as a stereotaxic positioner, a fixed gimbal or the like.

Referring again to FIG. 8, drive assembly 40 further includes a plurality of drive motors 170 coupled to arm 42 for rotation therewith. Pitch and yaw motors 156, 158 control the motion of arm 42 (and drive motors 170) about the X and Y axes and drive motors 170 control the motion of wrist unit 22 and surgical tool 24. Preferably, at least five drive motors 170 are coupled to arm 42 for providing at least five degrees of freedom to wrist unit 24. Drive motors 170 will preferably include encoders (not shown) for responding to servomechanism 16 and force sensors (not shown) for transmitting force and torque feedback to the surgeon S. As discussed above, the five degrees of freedom preferably include movement of carriage 122 and wrist unit 22 in the Z-direction, rotation of wrist unit 22 about the Z-axis, pitch and yaw rotation of surgical tool 62 around wrist 60 and actuation of tool 62.

As shown, cables 172 extend from each motor 170 around a motor drive pulley 174, an idler pulley 176 within arm 42 and along a relatively large pot capstan 178 to minimize the effect of friction torque on cables 172. The cables 172 each extend around another idler pulley 180 at distal end 48 of arm 42, around a coupling drive pulley 182 and back to the motor 170. The cables 172 will preferably be tensioned at the motor drive pulley 174 and anchored there as well as at the coupling drive pulley 182. As shown in FIG. 8, coupling drive pulley 182 is connected to a plurality of smaller pulleys 184 within coupling assembly 130 via a plurality of cables 186 for transferring motion from the motors 170 to wrist unit adaptor 52.

A method for performing a surgical procedure on a patient according to the present invention will now be described with reference to FIGS. 1–9. As shown in FIG. 2, mounting joints 30 are attached to receptacle 32, which is attached to the operating table O by sliding mounting arm 34 along rail 36. Each manipulator assembly 4 is then attached to its respective mounting joint 30 and articulated into the proper position and orientation relative to the patient P. Receptacles 32 are then coupled to servomechanism 16 and other systems that may be required during the surgical procedure, such as an RF power supply, a suction/irrigation system, etc. Sterile drapes 70 are placed over the manipulator assemblies 4 before, during or after the patient has been anesthetized (FIG. 3A). To prepare for the surgical procedure, manipulator assemblies 4 may or may not be chemically cleaned prior to covering them with drapes 70. Wrist unit adapters 52, cannula adapters 64 and scope adapters 110 are snapped onto forearm assemblies 46 of manipulator assemblies 4 (see FIGS. 3B and 5). The number and relative positions of scope adapters 110 and wrist unit adapters 52 will, of course, depend on the individual surgical procedure (e.g., cannula adapters 64 may not be required for open surgical procedures).

During the surgical procedure, surgical instrument assemblies 20 are coupled to their respective manipulator assemblies 4 by laterally urging each respective wrist unit shaft 56 through opening 80 of wrist unit adaptor 52. Each wrist unit 22 will have suitable identification means (not shown) to quickly and easily indicate what type of tool 24 is connected to the wrist unit 22. When the surgeon wishes to change surgical tools 24, he or she manipulates controller(s) 12 so that carriage 122 moves to a top or proximal position of travel along forearm assembly 46 (see FIG. 3B). In this position, surgical tool 24 is within cannula 66 or during open procedures, removed from the surgical site. The assistant(s) A then pulls upward on wrist cap 58 to release the latch (not shown), thereby allowing wrist unit 22 to slide further upwards and out of cannula 66. The assistant(s) A may then pull wrist unit 22 laterally to decouple it from wrist unit adaptor 52. When wrist unit 22 is no longer coupled to adaptor 52, the control mechanism understands that the system in is "tool change model", and drives carriage 122 to the proximal position if it hasn't already been moved there by the surgeon.

Figure 3B:
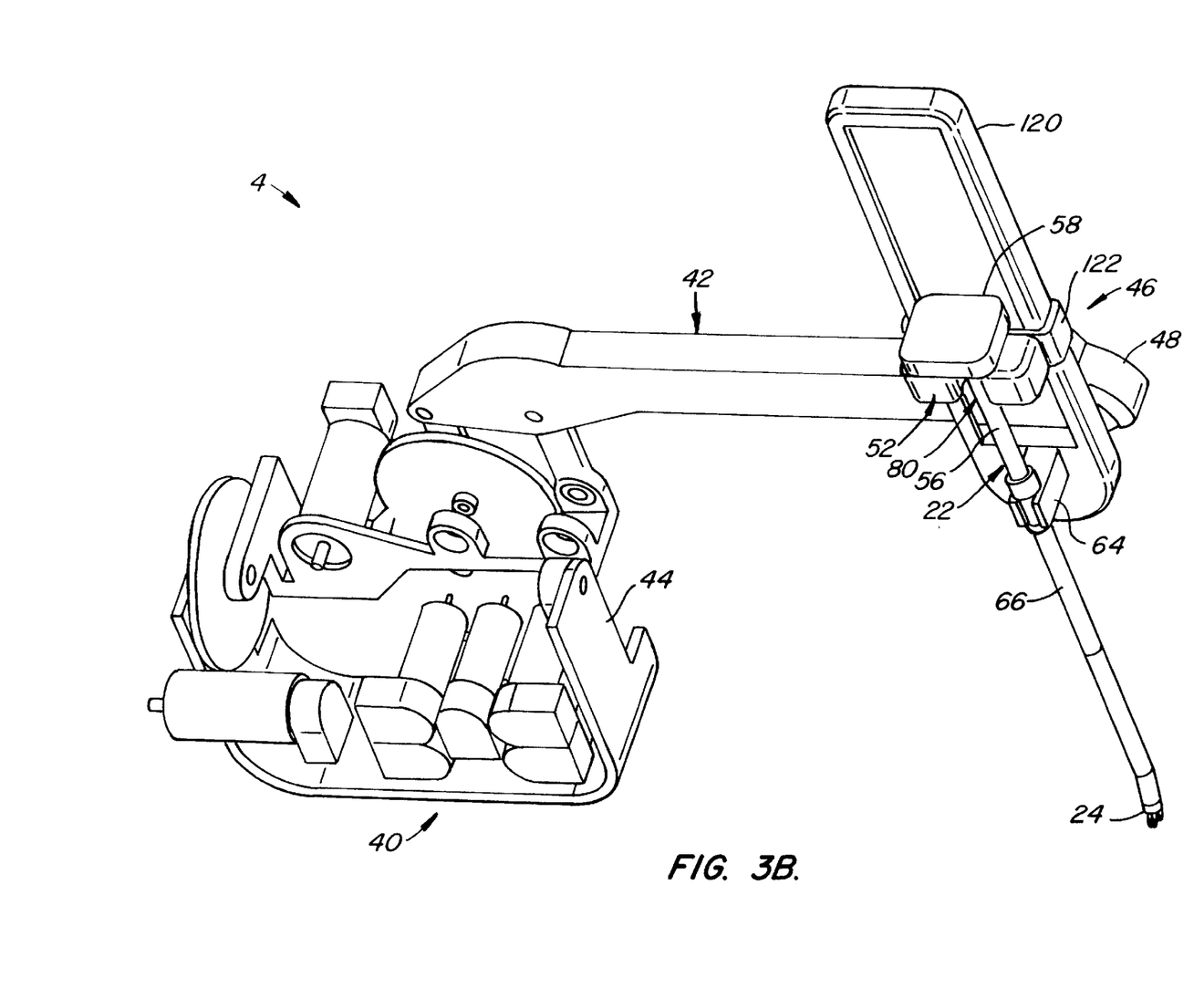
FIG. 3B is a perspective view of the robotic surgical manipulator without the sterile drape to illustrate a multiple degree of freedom arm coupling a driving assembly with a wrist unit and a surgical tool.

To couple another surgical instrument assembly 20 to manipulator assembly 4, the assistant(s) A grabs another assembly 20 from table T, laterally urges wrist unit shaft 56 into opening 80 of wrist unit adaptor 52, and then moves wrist unit 22 downward so that surgical tool 62 resides within cannula 66 (see FIGS. 1 and 3B). This downward movement of wrist unit 22 automatically mates the electrical couplings and motion feed-throughs (not shown) within wrist cap 58 and wrist unit adaptor 52. The system may include a control mechanism configured to lock carriage 122 travel at the top or proximal position, e.g., by actuating a brake (not shown), until the couplings are mated and wrist unit 22 is no longer being moved downward. At this point, the surgeon S may continue the surgical procedure.

The system and method of the present invention preferably includes a mechanism for counting the number of times wrist unit 22 is decoupled and coupled from wrist unit adaptor 52. In this manner, the manufacturer may limit the number of times wrist unit 22 can be used. In a specific configuration, an integrated circuit chip (not shown) is housed within wrist cap 58. The circuit chip counts the number of times wrist unit 22 is coupled to wrist unit adaptor 52, e.g., 20 times, and a warning shows up on the surgeon's console C. The control system then downgrades the performance of the system by reducing the load it can deliver or increasing apparent backlash.

What is claimed is:

1. A robotic surgical system for performing a procedure within a sterile field comprising:
   a surgical tool;
   a manipulator assembly including a manipulator arm having proximal and distal end portions;
   a sterile drape covering at least the manipulator arm of the manipulator assembly to shield the manipulator arm from the sterile field; and
   an adaptor for coupling the distal end portion of the manipulator arm with the surgical tool and transferring at least two degrees of motion from the manipulator assembly to the tool, the adaptor extending through the sterile drape and including one or more electrical connectors for transferring an electrical signal from the manipulator arm to the surgical tool and from the surgical tool to the manipulator arm.

2. The system of claim 1 wherein the surgical tool comprises an instrument.

3. The system of claim 1 wherein the surgical tool comprises an endoscope for viewing a treatment site.

4. The system of 1 wherein the adaptor is sterilizable, and includes an exposed portion on a side of the drape opposite the manipulator arm, the adaptor being attached to the manipulator arm such that the exposed portion remains sterile.

5. The system of claim 1 wherein the manipulator assembly further includes a drive assembly coupled to the proximal end portion of the manipulator arm for providing at least two degrees of freedom to the surgical tool, the sterile drape covering both the manipulator arm and the drive assembly to shield the arm and drive assembly from the sterile field.

6. The system of claim 1 further comprising a controller and means for sensing tactile sensations resulting from contact between the surgical tool and the patient and means for providing tactile feedback to the controller corresponding to the tactile sensations on the surgical tool.

7. A robotic surgical system for performing a procedure within a sterile field comprising:
   a surgical tool;
   a manipulator assembly including a manipulator arm having proximal and distal end portions;
   a sterile drape covering at least the manipulator arm of the manipulator assembly to shield the manipulator arm from the sterile field; and
   an adaptor for coupling the distal end portion of the manipulator arm with the surgical tool and transferring at least two degrees of motion from the manipulator assembly to the tool, the adaptor extending through the sterile drape and including one or more electrical connectors for transferring an electrical signal from the manipulator arm to the surgical tool and from the surgical tool to the manipulator arm;
   the tool comprising a surgical instrument, said instrument further comprising a wrist unit having a shaft with a distal wrist coupled to the instrument and a proximal end removably coupled to the adaptor.

8. The system of claim 7 wherein the wrist unit shaft and the instrument are rotatably coupled to the adaptor for rotation about a longitudinal axis of the shaft relative to the adaptor.

9. The system of 7 wherein the adaptor includes one or more motion feed-throughs for transferring motion from the manipulator assembly to the instrument.

10. The system of claim 9 wherein one of the motion feed-throughs provides rotation of the instrument about the distal wrist of the wrist unit.

11. The system of claim 9 wherein the surgical tool includes an end effector, one of the motion feed-throughs providing articulation of the end effector.

12. The system of claim 7 wherein the manipulator arm includes a remote center positioner constraining lateral movement of the wrist unit shaft to pivotal motion about a fixed spherical center of rotation at a point along the wrist unit shaft.

13. A robotic surgical system for performing a procedure within a sterile field comprising:
   a surgical tool;
   a manipulator assembly including a manipulator arm having proximal and distal end portions;
   a sterile drape covering at least the manipulator arm of the manipulator assembly to shield the manipulator arm from the sterile field;
   an adaptor for coupling the distal end portion of the manipulator arm with the surgical tool and transferring at least two degrees of motion from the manipulator assembly to the tool, the adaptor extending through the sterile drape;
   a cannula defining an inner lumen for receiving the surgical tool and providing access through a percutaneous penetration in the patient; and
   a sterilizable cannula adaptor extending through the drape and coupling the cannula to the distal end portion of the manipulator arm.

14. A robotic surgical system for performing a procedure within a sterile field comprising:
   a surgical tool, wherein the surgical tool is an instrument;
   a manipulator assembly including a manipulator arm having proximal and distal end portions;
   a sterile drape covering at least the manipulator arm of the manipulator assembly to shield the manipulator arm from the sterile field;
   an adaptor for coupling the distal end portion of the manipulator arm with the surgical tool and transferring at least two degrees of motion from the manipulator assembly to the tool, the adaptor extending through the sterile drape;
   a wrist unit having a shaft with a distal wrist coupled to the instrument and a proximal end removably coupled to the adaptor; and
   means for inhibiting the number of times which the wrist unit can be used in a surgical procedure.

15. The system of claim 14 wherein the limiting means includes means for counting each time the wrist unit is coupled to or decoupled from the adaptor.

16. A robotic surgical system for performing a procedure within a sterile field comprising:
- a surgical tool, wherein the surgical tool is an instrument;
- a manipulator assembly including a manipulator arm having proximal and distal end portions;
- a sterile drape covering at least the manipulator arm of the manipulator assembly to shield the manipulator arm from the sterile field;
- an adaptor for coupling the distal end portion of the manipulator arm with the surgical tool and transferring at least two degrees of motion from the manipulator assembly to the tool, the adaptor extending through the sterile drape;
- a wrist unit having a shaft with a distal wrist coupled to the instrument and a proximal end removably coupled to the adaptor; and
- a transmission unit coupled to the manipulator arm and covered by the sterile drape, the transmission unit having an axially movable carriage coupled to the adaptor and the wrist unit for axially reciprocating the adaptor, the wrist unit and the instrument.

17. The system of claim 16 wherein the transmission unit transmits at least three degrees of motion from the manipulator arm, through the adaptor to the wrist unit and the instrument, the degrees of motion including rotation of the wrist unit and the instrument relative to the adaptor, rotation of the instrument about the distal wrist of the wrist unit shaft and actuation of the end effector.

18. A telerobotic system for manipulating surgical tools at a surgical site within a sterile field comprising:
- a manipulator assembly including a manipulator arm having proximal and distal end portions;
- a sterile drape covering at least the manipulator arm of the manipulator assembly to shield the manipulator arm from the sterile field;
- an adaptor for coupling the distal end portion of the manipulator arm with the surgical tool and transferring at least two degrees of motion from the manipulator assembly to the tool, the adaptor extending through the sterile drape;
- one or more electrical connectors for transmitting electrical data signals between the controller and the surgical tool through the drape;
- a controller located in a remote position from the manipulator assembly; and
- a servomechanism coupling the controller to the manipulator arm for remote control of the manipulator arm.

19. The telerobotic system of claim 18 further comprising a viewing scope for viewing the surgical site, and a video display operatively coupled to the viewing scope for producing an image of the surgical site adjacent the controller.

20. The system of claim 18 further comprising means for sensing tactile sensations resulting from contact between the surgical tool and the patient and means for providing tactile feedback to the controller corresponding to the tactile sensations on the surgical tool.

21. The system of claim 18 wherein the adaptor is sterilizable and includes one or more motion feed-throughs for transferring motion from the manipulator assembly to the instrument, the adaptor further including an exposed portion on a side of the drape opposite the manipulator arm, the adaptor being attached to the manipulator arm such that the exposed portion remains sterile.

22. The system of claim 18 further comprising a wrist unit having a shaft with a distal wrist coupled to the instrument and a proximal end removably coupled to the adaptor, wherein the wrist unit shaft and the instrument are rotatably coupled to the adaptor for rotation about a longitudinal axis of the shaft relative to the adaptor.

23. The system of claim 18 wherein the manipulator assembly further includes a drive assembly coupled to the proximal end portion of the manipulator arm and the servomechanism for providing at least two degrees of freedom to the surgical tool, the sterile drape covering both the manipulator arm and the drive assembly to shield the arm and drive assembly from the sterile field.

24. A method for performing a surgical procedure within a sterile field with a robotic surgical system comprising:
- covering portions of a manipulator arm with a sterile drape to shield the arm from the sterile field;
- attaching a sterile adaptor to a distal end portion of the manipulator arm through the sterile drape;
- releasably coupling a sterile surgical tool to the robotic surgical system by coupling a tubular structure to the robotic surgical system, inserting an elongate shaft of the surgical tool through the tubular structure, and attaching the surgical tool to the adaptor; and
- introducing at least a portion of the tubular structure into an aperture in a body wall of the patient and introducing the surgical tool to a target site within the body of the patient.

25. The method of claim 24 wherein the sterile adaptor includes an exposed portion on a side of the drape opposite the manipulator arm, the sterile adaptor being attached to the manipulator arm such that the exposed portion remains sterile.

26. The method of claim 24 articulating the surgical tool with a drive assembly coupled to a proximal end portion of the manipulator arm and shielding the drive assembly from the sterile field with the sterile drape.

27. The method of claim 24 further comprising transferring motion of the manipulator arm through the adaptor to the instrument.

28. The method of claim 24 further comprising removably coupling a wrist unit to the adaptor and attaching a surgical instrument to a distal wrist of the wrist unit.

29. The method of claim 28 further comprising pivoting the instrument about the distal wrist in response to input from the manipulator assembly.

30. The method of claim 28 further comprising rotating the wrist unit and the instrument about the shaft axis and articulating an end effector on the instrument in response to input from the manipulator assembly.

31. The method of claim 24 further comprising constraining movement of the surgical tool about a fixed spherical center of rotation.

32. The method of claim 24 further comprising remotely controlling movement of the manipulator arm with an input device.

33. The method of claim 32 further comprising viewing an image of the target site on a video display remotely positioned from the target site.

34. The method of claim 24, wherein said surgical tool is introduced into the patient by inserting the portion of the tubular structure into said aperture, and then inserting said surgical tool into said aperture through said tubular structure.

35. The method of claim 24, further comprising exchanging said surgical tool for a second surgical tool, wherein the portion of the tubular structure remains in the aperture during the tool exchanging step.

36. A method for performing a surgical procedure within a sterile field with a robotic surgical system comprising:

covering portions of a manipulator arm with a sterile drape to shield the arm from the sterile field;

attaching a sterile adaptor to a distal end portion of the manipulator arm through the sterile drape;

attaching a sterile surgical tool to the adaptor;

introducing the surgical tool to a target site on the patient with the manipulator arm; and transmitting one or more electrical signals through the adaptor between the manipulator arm and the surgical tool.

37. The method of claim 36, wherein a shaft of a wrist unit is coupled to the manipulator arm and a wrist of the wrist unit is coupled to the surgical tool, and further comprising constraining lateral movement of the wrist unit shaft to pivotal motion about a fixed spherical center of rotation at a point along the wrist unit shaft with a remote center positioner.

38. A method for performing a surgical procedure within a sterile field with a robotic surgical system comprising:

covering portions of a manipulator arm with a sterile drape to shield the arm from the sterile field;

attaching a sterile adaptor to a distal end portion of the manipulator arm through the sterile drape;

attaching a sterile surgical tool to the adaptor;

attaching a sterile cannula adaptor through the sterile drape to the distal end portion of the manipulator arm;

attaching a cannula to the cannula adaptor;

introducing a surgical instrument through the cannula into a body cavity in the patient; and introducing the surgical tool to a target site on the patient with the manipulator arm.

39. A method for performing a surgical procedure within a sterile field with a robotic surgical system comprising:

covering portions of a manipulator arm with a sterile drape to shield the arm from the sterile field;

attaching a sterile adaptor to a distal end portion of the manipulator arm through the sterile drape;

attaching a sterile surgical tool to the adaptor by removably coupling a wrist unit to the adaptor and attaching a surgical instrument to a distal wrist of the wrist unit;

introducing the surgical tool to a target site on the patient with the manipulator arm; and limiting a number of times which the wrist unit is used in a surgical procedure.

40. The method of claim 39 wherein the limiting step includes counting each time the wrist unit is coupled to the adaptor.

41. A method for performing a surgical procedure within a sterile field with a robotic surgical system comprising:

covering portions of a manipulator arm with a sterile drape to shield the arm from the sterile field;

attaching a sterile adaptor to a distal end portion of the manipulator arm through the sterile drape by coupling the adaptor to a movable carriage on the manipulator arm, the carriage being covered by the sterile drape;

attaching a sterile surgical tool to the adaptor;

introducing the surgical tool to a target site on the patient with the manipulator arm; and axially moving the carriage to axially move the surgical tool relative to the manipulator arm.

* * * * *